(12) United States Patent
Stephens et al.

(10) Patent No.: US 12,194,126 B2
(45) Date of Patent: *Jan. 14, 2025

(54) SHAVING AID COMPRISING A BENEFIT AGENT

(71) Applicant: The Gillette Company LLC, Boston, MA (US)

(72) Inventors: Alison Fiona Stephens, Cookham (GB); Valerie Jean Bradford, Framingham, MA (US); Joia Kirin Spooner-Fleming, Jamaica Plain, MA (US)

(73) Assignee: The Gillette Company LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/551,982

(22) Filed: Dec. 15, 2021

(65) Prior Publication Data

US 2022/0202677 A1    Jun. 30, 2022

Related U.S. Application Data

(60) Provisional application No. 63/131,374, filed on Dec. 29, 2020.

(51) Int. Cl.
| | |
|---|---|
| *A61K 8/49* | (2006.01) |
| *A61K 8/02* | (2006.01) |
| *A61K 8/81* | (2006.01) |
| *A61Q 9/02* | (2006.01) |
| *B26B 21/22* | (2006.01) |

(52) U.S. Cl.
CPC .......... *A61K 8/4953* (2013.01); *A61K 8/0283* (2013.01); *A61K 8/8111* (2013.01); *A61Q 9/02* (2013.01); *B26B 21/22* (2013.01)

(58) Field of Classification Search
CPC .. A61K 8/4953; A61K 8/0283; A61K 8/8111; A61Q 9/02; B26B 21/22
See application file for complete search history.

(56) References Cited

U.S. PATENT DOCUMENTS

| | | |
|---|---|---|
| 2,838,442 A | 6/1958 | Theodore |
| 5,113,585 A | 5/1992 | Rogers |
| 5,349,750 A | 9/1994 | Tseng |

(Continued)

FOREIGN PATENT DOCUMENTS

| | | |
|---|---|---|
| CN | 1984950 A | 6/2007 |
| CN | 103260587 A | 8/2013 |

(Continued)

OTHER PUBLICATIONS

All Office Actions; U.S. Appl. No. 16/864,198, filed May 1, 2020.

(Continued)

*Primary Examiner* — Jianfeng Song
(74) *Attorney, Agent, or Firm* — Andres E. Velarde; Kevin C. Johnson

(57) ABSTRACT

A shaving aid including a lubricant and a benefit agent. The benefit agent is azoxystrobin. Also provided is hair removal device with a shaving aid and the shaving aid includes azoxystrobin. The shaving aid may be on-board the hair removal device or provided separately. The shaving aid may be a solid or a liquid.

8 Claims, 5 Drawing Sheets

(56) References Cited

U.S. PATENT DOCUMENTS

| | | | |
|---|---|---|---|
| 5,906,997 A | 5/1999 | Schwartz et al. | |
| 6,161,288 A | 12/2000 | Andrews | |
| 6,298,558 B1 | 10/2001 | Tseng | |
| 6,301,785 B1 | 10/2001 | Kwiecien et al. | |
| 6,449,849 B1 | 9/2002 | Hackerman | |
| 7,024,776 B2 | 4/2006 | Wain | |
| 7,197,825 B2 | 4/2007 | Walker et al. | |
| 7,607,230 B2 | 10/2009 | Aviza et al. | |
| 8,236,214 B2 | 8/2012 | Kwiecien | |
| 9,119,796 B2 | 9/2015 | Cook et al. | |
| 9,216,514 B2 | 12/2015 | Bridges et al. | |
| 10,675,772 B2 | 6/2020 | Fontecchio et al. | |
| 10,682,778 B2 | 6/2020 | Hayes et al. | |
| 2006/0018968 A1 | 1/2006 | Melbouci | |
| 2006/0035861 A1 | 2/2006 | Berg et al. | |
| 2006/0225285 A1* | 10/2006 | Slavtcheff | C11D 1/126 30/41 |
| 2006/0275238 A1 | 12/2006 | Blasko-Begoihn et al. | |
| 2007/0254947 A1 | 11/2007 | Takiguchi et al. | |
| 2008/0034590 A1 | 2/2008 | Prudden et al. | |
| 2008/0060201 A1 | 3/2008 | Kwiecien | |
| 2008/0254209 A1 | 10/2008 | Dorgan | |
| 2009/0049695 A1 | 2/2009 | Keene et al. | |
| 2011/0041865 A1 | 2/2011 | Stephens et al. | |
| 2011/0197447 A1 | 8/2011 | Stephens et al. | |
| 2012/0023763 A1 | 2/2012 | Ariyanayagam et al. | |
| 2012/0087981 A1 | 4/2012 | Wang et al. | |
| 2012/0094006 A1 | 4/2012 | Kwiecien | |
| 2012/0097981 A1 | 4/2012 | Chang | |
| 2013/0042482 A1 | 2/2013 | Bradford et al. | |
| 2013/0121937 A1 | 5/2013 | Kim | |
| 2014/0366381 A1 | 12/2014 | Phipps et al. | |
| 2016/0143836 A1* | 5/2016 | Hayes | A61K 8/86 30/32 |
| 2016/0199990 A1 | 7/2016 | Nicholas et al. | |
| 2017/0000721 A1 | 1/2017 | Bradford et al. | |
| 2017/0334082 A1 | 11/2017 | Hayes et al. | |
| 2018/0001494 A1* | 1/2018 | Stephens | A61K 8/891 |
| 2018/0001495 A1 | 1/2018 | Stephens et al. | |
| 2018/0117780 A1 | 5/2018 | Moloney et al. | |
| 2019/0216710 A1 | 7/2019 | Smith | |
| 2020/0353634 A1 | 11/2020 | Stephens et al. | |
| 2021/0069091 A1* | 3/2021 | Oh | A61K 8/27 |
| 2021/0283131 A1* | 9/2021 | Richards | A61K 8/4926 |
| 2021/0401710 A1* | 12/2021 | Johnson | A61K 8/89 |

FOREIGN PATENT DOCUMENTS

| | | | | |
|---|---|---|---|---|
| CN | 104498551 A | 4/2015 | | |
| CN | 107308071 A | 11/2017 | | |
| CN | 107889453 A | 4/2018 | | |
| CN | 109280204 A | 1/2019 | | |
| DE | 102005026711 A1 * | 2/2007 | | A61K 8/0212 |
| EP | 1630525 A2 | 3/2006 | | |
| JP | 2013139422 A | 7/2013 | | |
| WO | 2013111979 A1 | 8/2013 | | |
| WO | WO-2018023128 A1 * | 2/2018 | | A01N 25/04 |

OTHER PUBLICATIONS

All Office Actions; U.S. Appl. No. 17/944,839, filed Sep. 14, 20223.
Cekol 30000 P (a href="https://www.signetexcipients.com/Content/Upload/949Xt9Cekol30000PPDS.pdf" target="_blank"https://www.signetexcipients.com/Content/Upload/949Xt9Cekol30000PPDS.pdf/ a) available Sep. 22, 2009, pp. 1-2. (Year: 2009).
Choi et al., "Promotion Effects of Ultra-High Molecular Weight Poly-y-Glutamic Acid on Wound Healing", Jornal of Microbiology and Biotechnology, vol. 25, No. 6, Mar. 20, 2015, pp. 941-945.
Lee et al., "In vitro evaluation of new functional properties of poly-y-glutamic acid produced by Bacillus Subtilis D7", Saudi Journal of Biological Science, vol. 21, Sep. 17, 2013, pp. 153-158.
Unpublished U.S. Appl. No. 17/944,839, filed Sep. 14, 2022, to Alexander Shih Lee et al.
All Office Actions; U.S. Appl. No. 18/239,144, filed Aug. 29, 2023.
Particle Size / Mesh Conversion Chart, online retrieved from "https://www.powdertechnologyinc.com/particle-size-mesh-conversion-chart/", on Jun. 29, 2023.
Unpublished U.S. Appl. No. 18/239,144, filed Aug. 29, 2023, Alexander Shih Lee et al.

* cited by examiner

SHAVING AID COMPRISING A BENEFIT AGENT

FIELD OF THE INVENTION

The present disclosure is directed to a shaving aid comprising a benefit agent comprising an azoxystrobin, another strobilurin or combinations thereof. The invention is also directed to a hair removal device that includes the shaving aid.

BACKGROUND OF THE INVENTION

Hair removal devices such as razors and hair removal heads such as razor cartridges often incorporate shaving aids to provide lubrication benefits during use. Hair removal devices such as razors include one-piece razors which include a hair removal head and a handle as a single unit, or shaving systems in which the hair removal head is attachable/detachable to/from the handle. Shaving aids may include a lubricant and a carrier matrix such as a structurant or polymer matrix in which the lubricant is dispersed. Alternately, the lubricant may comprise a major portion of the shaving aid and the shaving aid may lack a carrier matrix, such as in pressed-pellet type shaving aids, or shaving aids included in a container. Shaving aids that include a polymer matrix may include extruded shaving aids in which the carrier matrix material is a polymer. Shaving aids that include a structurant may include melt-formed shaving aids in which the carrier matrix material is a non-polymeric room-temperature solid.

Shaving aids can also take a variety of forms. One common form is the lubristrip, which is typically integrated into the hair removal head such as the cartridge of a razor to provide lubrication during shaving. Another common form is a "wing" or "soap wing" which are disposed outward of the cartridge, and generally attached to it. Other common forms include pressed powders such as tablets and liquid shaving aids that may be used separately from the hair removal device or dispensed from a container within the hair removal device. Where the shaving aid is a solid the container may take the form of a box or tray with at least one aperture or open side or end to allow the shaving aid to be released from the container.

Where the shaving aid is a liquid, the container may take the form of a reservoir on-board the hair removal device with at least one aperture or means by which to release the shaving aid from the reservoir and onto the skin. The shaving aid may be dispensed directly from the reservoir onto the skin surface (e.g. face or body) to be treated (e.g. shaved). For example, the shaving aid may be dispensed adjacent to the hair removal head. Embodiments of such a configuration are depicted in U.S. Pat. Nos. 8,745,877, 10,800,058, 10,856,641, and 10,035,275, Alternately, the liquid shaving aid may be dispensed elsewise, such as from the end of the hair removal device remote from the hair removal head. For example, the shaving aid may be dispensed onto the hand for subsequent application to the surface to be treated. Embodiments of such a configuration are depicted in US2018/0297220, US2018/0297225, US2018/0297222, US2018/0297223, and US2018/0297221.

The container (e.g. the reservoir or tray/box) may be removeable and/or refillable and/or replaceable.

The lubricant is most commonly composed, at least partly, of polyethylene oxide (PEO), also called POLYOX™ (Dow Chemical). PEO is a high molecular weight water soluble polymer. When activated by water during the shave cycle, the PEO deposits onto the skin, adding a layer of lubrication. PEO in water is a viscoelastic fluid, and the rheological properties are directly correlated to the coefficient of friction (CoF) of the fluid. As the molecular weight of the polymer increases, the viscoelastic fluid properties increase as well, which can lead to a lower CoF.

The lubrication provided by the lubricant is important to mitigating negatives typically associated with shaving including tug, pull, and skin irritation. Further, additional benefit agents can be incorporated into the shaving aid that may further mitigate these and/or other negatives by being deposited and delivered to the skin. Skin benefit agents that may be desirably included in shaving aids to deliver during shaving include moisturizers, astringents, warming/cooling sensates, irritation-mitigators, and many such embodiments are known in the art. Despite the advent of skin benefit agents, including anti-irritation benefit agents, skin irritation from shaving remains a dominant consumer negative associated with shaving, depilation and other hair-removal processes and devices. As such, shaving aids that include improved anti-irritation benefit agents and hair removal devices comprising shaving aids that include improved anti-irritation benefit agents are required.

SUMMARY OF THE INVENTION

The present disclosure provides a shaving aid, suitable for use with a hair removal device, comprising a lubricant and a skin benefit agent that includes an azoxystrobin, another strobilurin or combinations thereof.

The lubricant may comprise at least 50% polyethylene oxide.

The shaving aid may further comprise a matrix polymer.

The azoxystrobin may be disposed at least partly within the lubricant

The matrix polymer may be ethylene vinyl acetate.

The matrix polymer may have a glass-transition temperature less than 130° C.

The shaving aid may further comprise a non-polymeric matrix.

The azoxystrobin may be disposed at least partly within the lubricant

The non-polymeric matrix may have a melt-temperature less than 100° C.

The shaving aid may comprise about 0.1% to about 5%, by weight of the shaving aid, of azoxystrobin The present disclosure is also directed to a hair removal device comprising a hair removal head and the shaving aid wherein the shaving aid comprises a lubricant and benefit agent comprising azoxystrobin.

The hair removal device may be a razor.

The shaving aid may be a liquid and contained within a reservoir on-board the hair removal device. The shaving aid may be dispensed adjacent to the hair removal head. The shaving aid may be dispensed opposite to the hair removal head.

The shaving aid may be a solid and contained within a container on-board the hair removal device.

The present disclosure is also directed to a hair removal device comprising a shaving aid on-board the hair removal device, wherein the shaving aid comprises a lubricant and a strobilurin.

The lubricant may comprise at least 50% polyethylene oxide.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements.

DETAILED DESCRIPTION

The present disclosure relates to a shaving aid suitable for use with a hair removal device, in which the shaving aid includes a benefit agent comprising azoxystrobin, the strobilurins or combinations thereof. Without wishing to be bound by theory, it is believed that the shaving aid compositions of the present disclosure help mitigate irritation experienced during and/or after shaving.

Hair Removal Device

According to some examples of the disclosure, the shaving aid finds particular application for hair removal devices. Hair removal devices generally comprise a hair removal head and a handle 30 and/or grip portion, upon which the hair removal head is mounted, either permanently or detachably/attachably. The hair removal device can be manual or power driven and can be used for wet and/or dry application. In some examples, the hair removal head may include a wide scraping surface, such as where the hair removal device is used with a depilatory, or a foil where the device is a shaving razor. In other examples, with reference to FIG. 1, the hair removal head may be a razor cartridge 10.

The hair removal head may be pivotally connected to a connecting structure 50 that in turn, or independently (e.g. permanently fixed), is connected to a handle 30. In some examples, the connecting structure 50 includes at least one arm 32 to releasably engage the hair removal head. The hair removal head may be integral with the handle 30 so that the hair removal device is discarded as a whole unit, or may comprise a detachable hair removal head that forms part of a shaving system, in which the detachable hair removal head is uncoupled from the handle 30 and disposed of and a new detachable hair removal head is coupled to the same handle.

Figure 1:
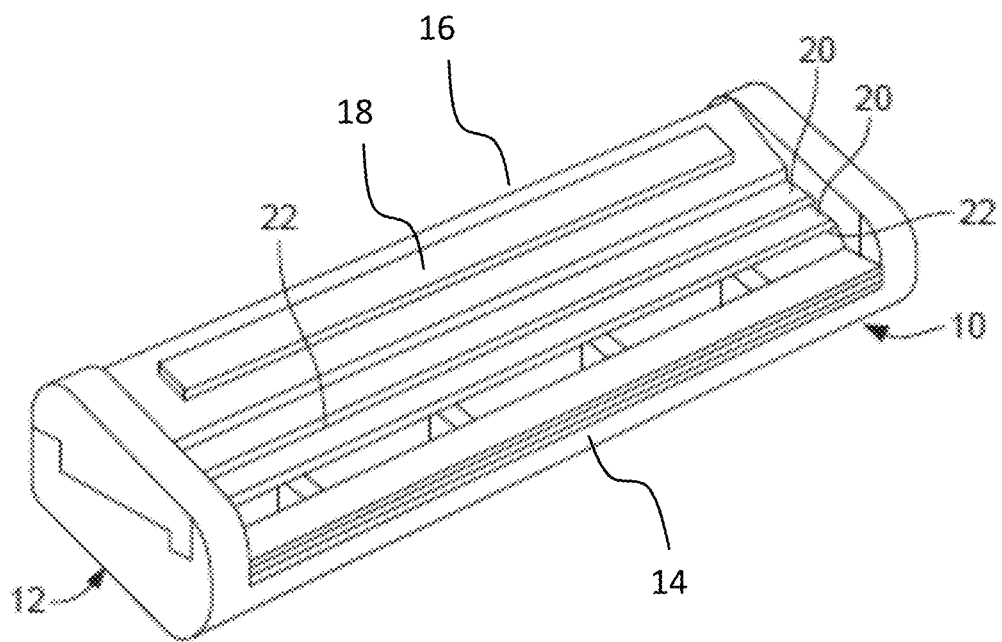
FIG. 1 is a perspective view of a razor cartridge 10 comprising a shaving aid in accordance with the present disclosure.
Figure 2A:
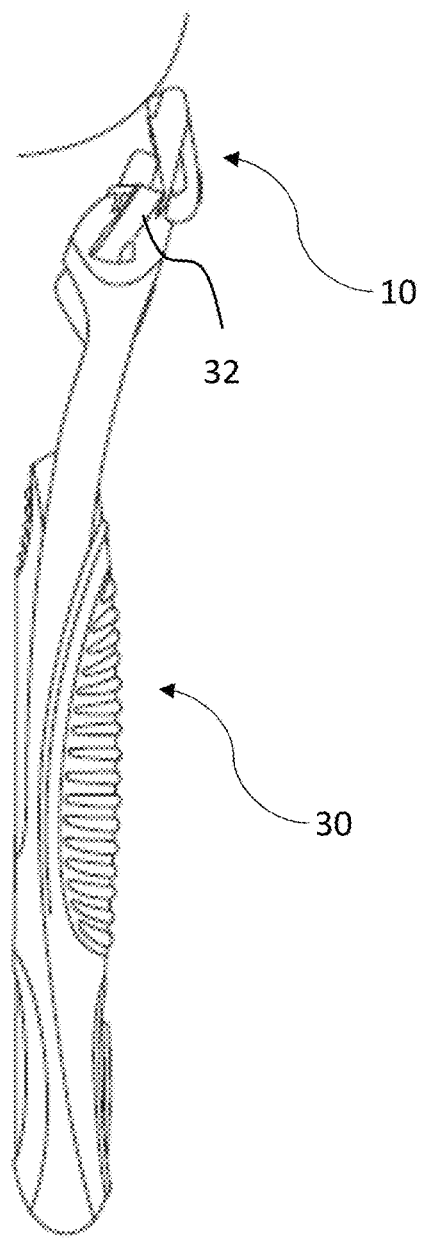
FIG. 2a is a side view of a razor comprising a shaving aid in the form of a lubristrip in accordance with the present disclosure.
Figure 2B:
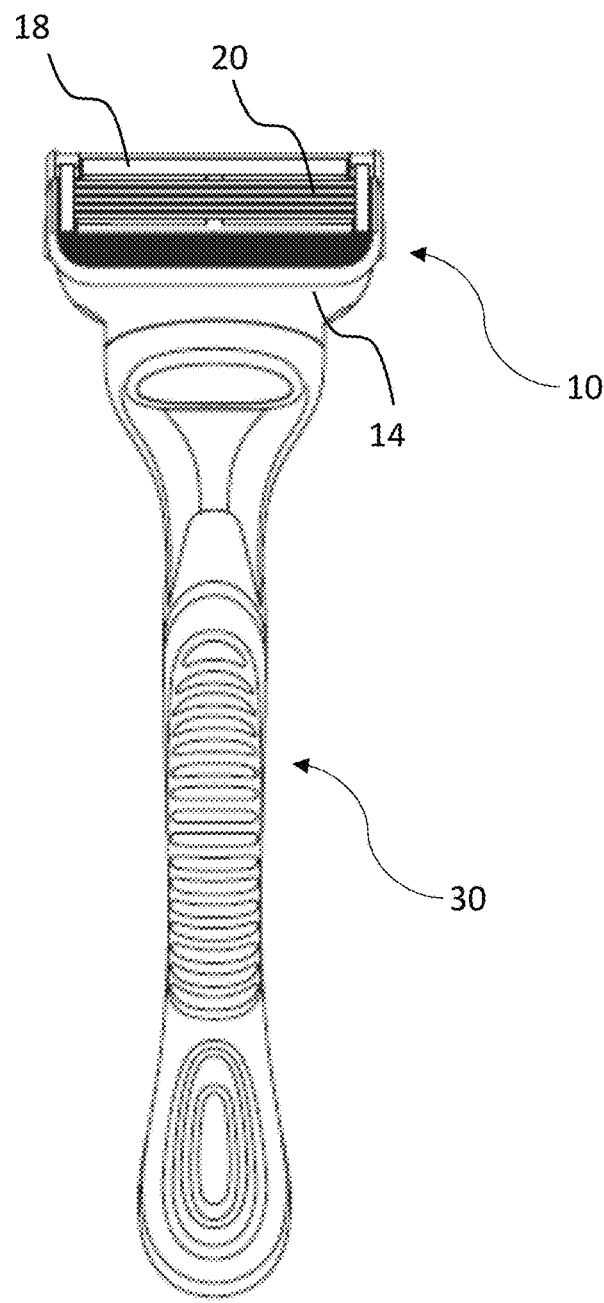
FIG. 2b is a front view of a razor comprising a shaving aid in the form of a lubristrip in accordance with the present disclosure.
Figure 3A:
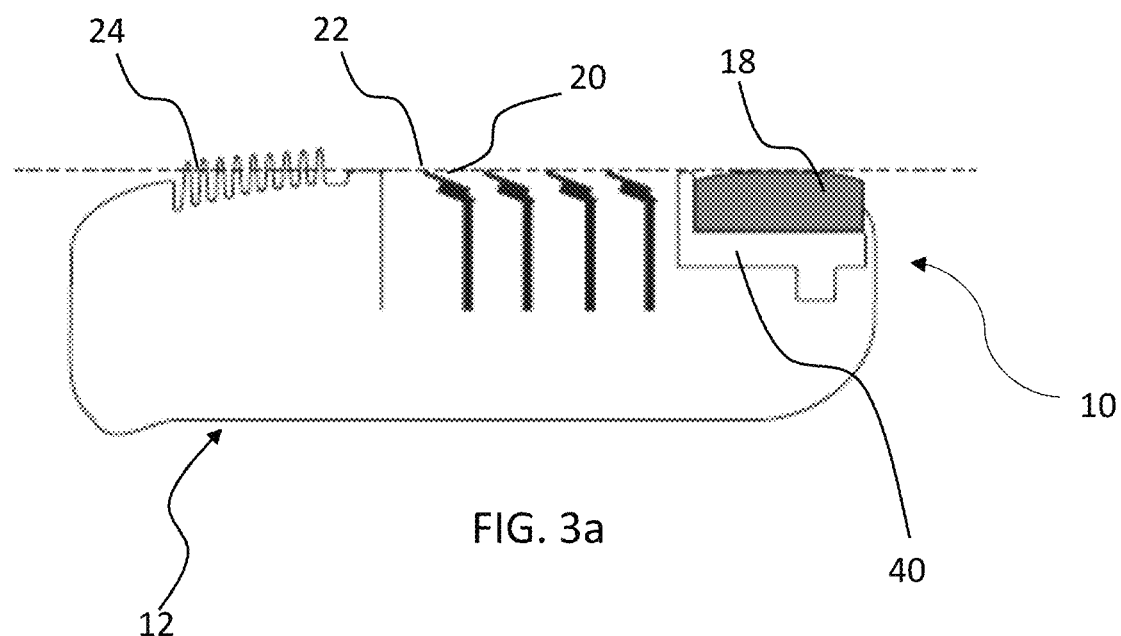
FIG. 3a is a cut-through view of a razor cartridge 10 comprising a shaving aid in the form of a solid contained within a box or tray in accordance with the present disclosure.
Figure 3B:
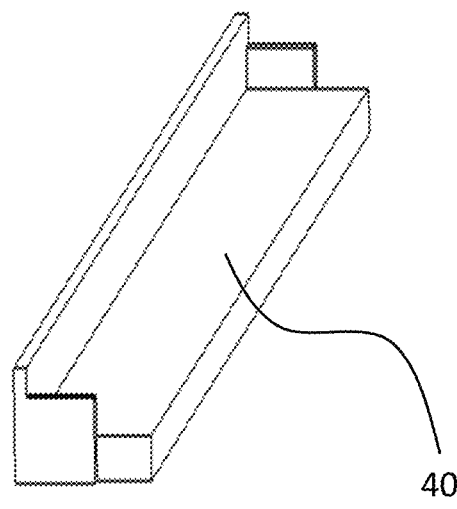
FIG. 3b is a perspective view of a tray that may contain the solid shaving aid.
Figure 3C:
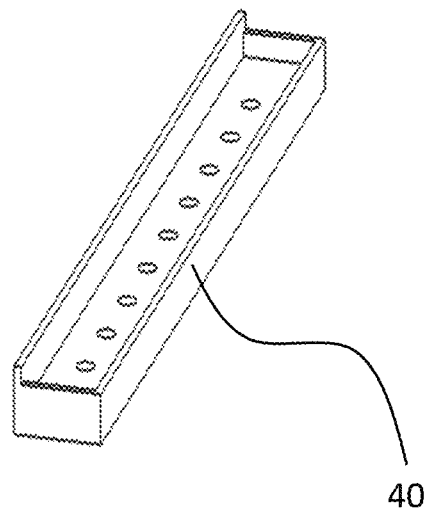
FIG. 3c is a perspective view of a box that may contain the solid shaving aid.
Figure 4A:
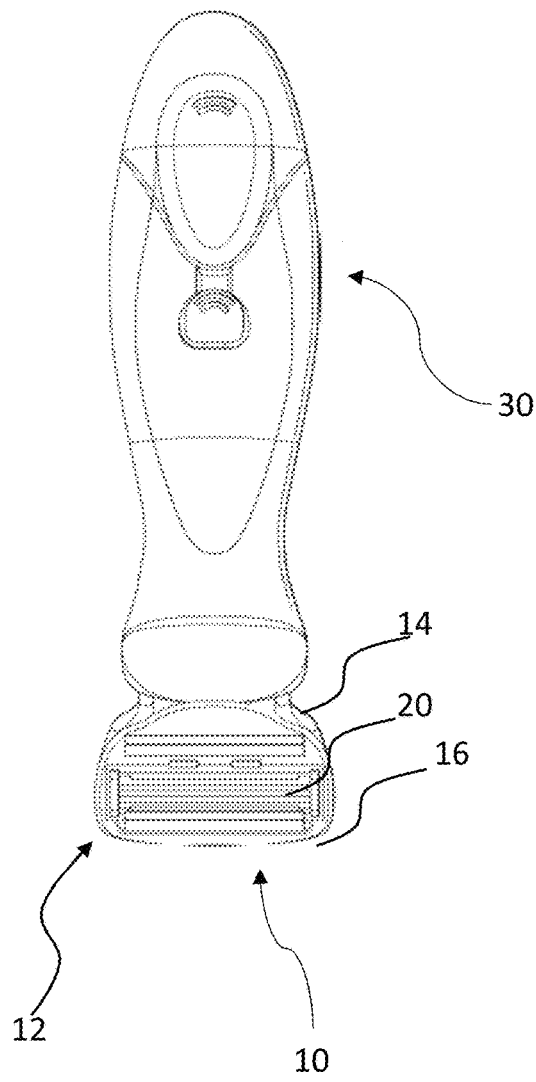
FIG. 4a is a front view of a shaving system comprising a reservoir for dispensing a liquid shaving aid in accordance with the present disclosure where the shaving aid is dispensed directly onto the skin surface being treated.
Figure 4B:
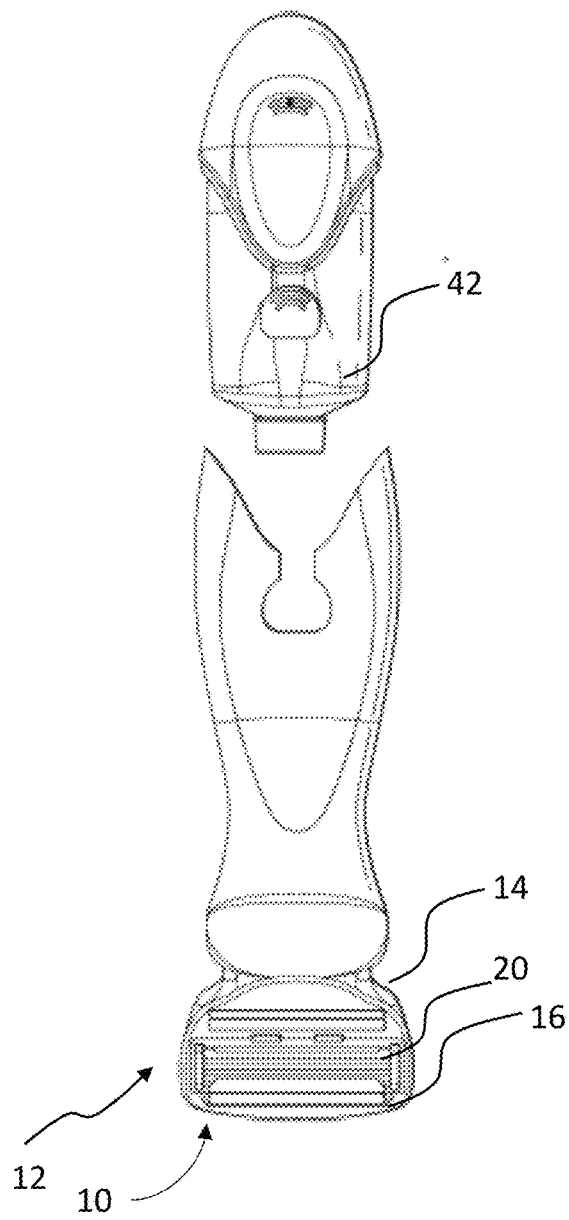
FIG. 4b is an exploded view of a shaving system comprising a reservoir for dispensing a liquid shaving aid in accordance with the present disclosure where the shaving aid is dispensed directly onto the skin surface being treated.
Figure 5A:
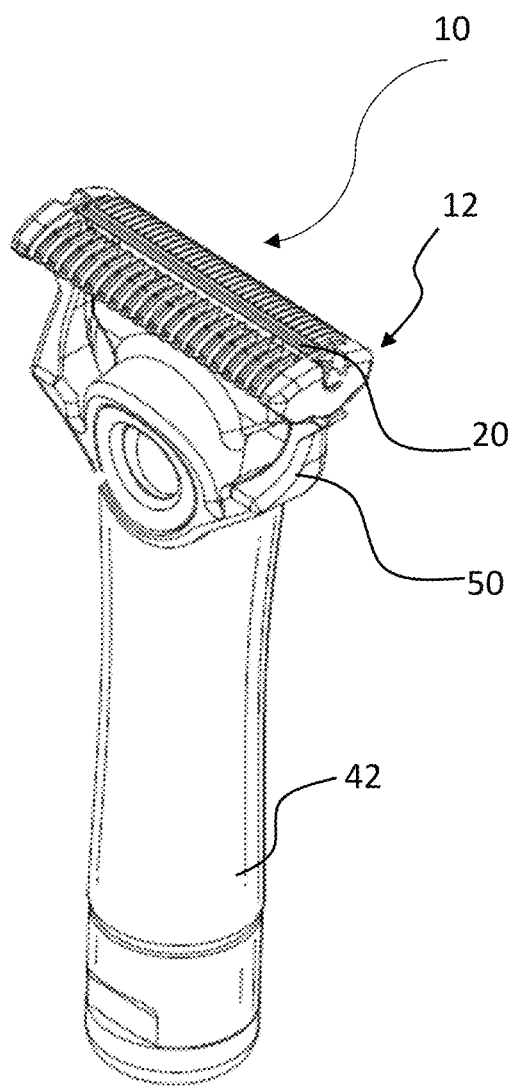
FIG. 5a is a perspective view of a shaving system comprising a reservoir for dispensing a liquid shaving aid in accordance with the present disclosure where the shaving aid is not dispensed directly onto the skin surface being treated.
Figure 5B:
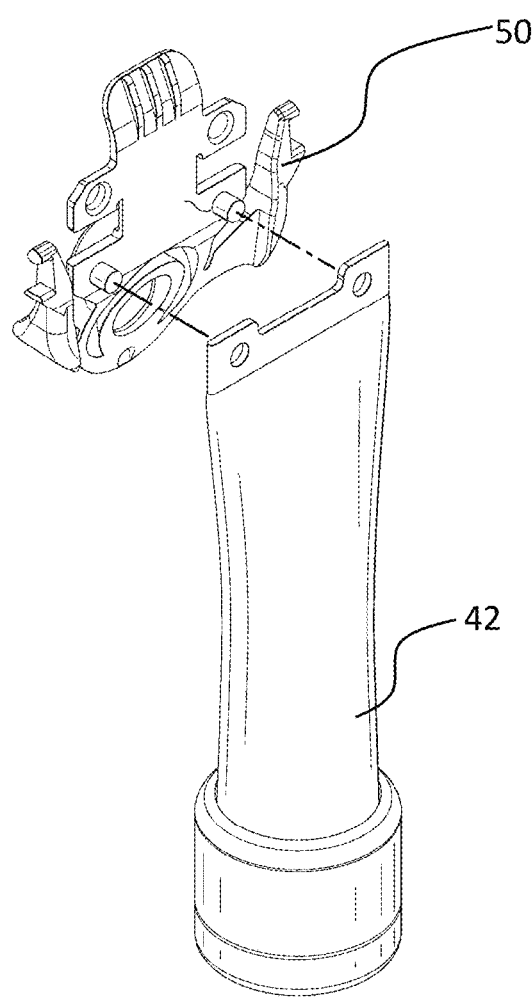
FIG. 5b is an exploded view of a shaving system comprising a reservoir for dispensing a liquid shaving aid in accordance with the present disclosure where the shaving aid is dispensed not directly onto the skin surface being treated and the shaving system comprises a connecting structure and a reservoir as separate components of the system.

The hair removal head typically comprises one or more elongated edges usually positioned between a first and second end, the one or more elongated edges comprising a tip extending forwardly. With reference to FIG. 1, where the hair removal head is a razor cartridge 10, the cartridge 10 may comprise a housing 12, and the one or more elongated edges can include one or more razor blades 20 incorporated into the housing 12, in which each blade 20 includes a blade edge 22.

A variety of razor cartridges can be used in accordance with the present disclosure. For example, U.S. Pat. No. 7,168,173 generally describes a FUSION® razor that is commercially available from The Gillette Company and which includes a razor cartridge with multiple blades. Non limiting examples of suitable razor cartridges, with and without fins, guards, and/or shave aids, include those marketed by The Gillette Company under the FUSION®, VENUS® product lines (Gillette) as well as those disclosed in U.S. Pat. Nos. 7,197,825, 6,449,849, 6,442,839, 6,301,785, 6,298,558, 6,161,288, and U.S. Patent Application Publication No. 2008/060201. Those of skill in the art will understand that the shaving aid can be used with any currently marketed razor or shaving system, including those having 2, 3, 4 or more blades. In such a case, the hair removal device is a razor, the hair removal head is a razor cartridge 10, and the one or more elongated edges are blades. Another example of a hair removal device is a scraping tool for use with a hair removal composition, i.e., a depilatory.

In some examples, at least one shaving aid is located on a portion of the cartridge 10 that contacts skin during the hair removal process, forward and/or aft of the blades 20. A feature "forward" of the one or more elongated edges, for example, is positioned so that the surface to be treated by the hair removal device encounters the feature before it encounters the elongated edges. A feature "aft" of the elongated edge is positioned so that the surface to be treated by the hair removal device encounters the feature after it encounters the elongated edges.

In the example shown in FIG. 1, a shaving aid 18 is positioned on a cap 16 of the razor cartridge 10. In other examples, a plurality of shaving aids may be provided on the hair removal head, in which the plurality of shaving aids may be the same (identical) or different in terms of physical shape/structure and/or chemical composition. These shaving aids may be placed collectively (for example adjacent to one another) ahead of or behind the elongated edges (e.g. blades on a razor cartridge), including side by side, or separately with one ahead of the elongated edges and the other behind.

The shaving aid may be separate from or attached to the hair removal device or head. The shaving aid may be attached to the hair removal device or head by any suitable attachment means such as adhesive or interference fit or may be contained at least partially within a container 40. Exemplary embodiments of solid shaving aids contained in containers include US2011/0041865 and US2012/0023763. The shaving aid may be formed in the container 40 by any means. The shaving aid may be compressed directly in the container 40.

In some examples, as shown in FIG. 1, the cartridge 10 comprises a guard 14 comprising at least one elongated flexible protrusion (not labeled) to engage a user's skin. The at least one flexible protrusion may comprise flexible fins generally parallel to the one or more elongated edges. The at least one flexible protrusion may additionally or alternatively comprise flexible fins comprising at least one portion which is not generally parallel to the one or more elongated edges. Non-limiting examples of suitable guards include those used in current razor blades and include those disclosed in U.S. Pat. Nos. 7,607,230 and 7,024,776; (disclosing elastomeric/flexible fin bars); and U.S. Patent Application Publication Nos. 2008/0034590 (disclosing curved guard fins) and 2009/0049695A1 (disclosing an elastomeric guard having guard forming at least one passage extending between an upper surface and a lower surface). In some examples, the shaving aid is positioned on the cartridge 10 aft of the guard and forward of the elongated edge. In another example, the shaving aid is positioned on the cartridge 10 forward of the guard. This example can be particularly useful to deliver the shaving aid prior to contact with the guard.

The hair removal device may include a liquid shaving aid contained in a container such as a reservoir 42 on-board the hair removal device. Exemplary embodiments of hair removal devices with liquid shaving aids contained in a reservoir 42 that dispense the shaving aid to the surface to be shaved include U.S. Pat. Nos. 7,007,389, 6,308,413, 4,753,006, 4,635,361, 6,986,207, 5,855,066 and 4,129,942. Such dispensing razors have been described as being capable of dispensing various types of shaving related preparations, including clear or translucent shaving gels or lotions. Compositions intended for liquid dispensing in addition to providing lubrication also need to ensure the desired viscosity. For example, a less viscous formulation may be desirable in certain instances, such as where the formulator wants the composition to dispense in a discrete area but quickly spread to contact and/or coat a large surface, such as the shaving head and cutters. It can also be desirable, however, for the product to be sufficiently thick so it will not run off or otherwise be pushed away from the portion of skin desired for treatment. Many different types of thickeners and viscosity modifying agents can impact the viscosity and rheology of the composition. Many of these ingredients, however, also impact other characteristics of the composition when added, such as making the composition stringy or tacky, or making the composition cloudy or opaque which may not be desirable in certain embodiments. Additional exemplary embodiments of dispensing razors may incorporate additional features such as a locking tab to secure the reservoir 42 to the hair removal device (U.S. Pat. No. 10,800,058), a gripping sleeve (U.S. Pat. No. 10,688,675), a piercer to puncture a seal on a replaceable reservoir (U.S. 2019/036a78) and a support surface (U.S. 2019/0365079).

Water Soluble Polymer

The shaving aid may comprise a lubricant comprising a water soluble polymer, which provides lubrication during the shave once the water soluble polymer forms at least a partial solution with water. Examples of suitable water soluble polymers may include polyethylene oxide (PEO), polyvinyl pyrrolidone, polyacrylamide, polyhydroxymethacrylate, polyvinyl imidazoline, polyethylene glycol (PEG), polyvinyl alcohol, polyhydroxyethymethacrylate, copolymers of PEO and polypropylene oxide (PPO), guars, celluloses, modified celluloses, and mixtures thereof. Preferably, the water soluble polymer is PEO, and in some examples, the water soluble polymer may be selected from high and/or low molecular weight PEO referred to in the industry as PEO and PEG respectively.

According to the present disclosure, the shaving aid may comprise a lubricant comprising from about 1% to about 99% by weight of the shaving aid, preferably at least about 15%, more preferably at least about 20%, most preferably at least about 25%, and up to about 70%, preferably up to about 60% by weight of the shaving aid. The lubricating material preferably comprises at least 50% PEO by weight of the lubricant.

The water soluble polymer (especially PEO) may have a number-average molecular weight of at least about 20,000 g/mol, preferably at least about 50,000, more preferably at least about 100,000 or from about 100,000 to about 10 million, or about 300,000 to about 8 million, or from about 1 million to about 5 million or about 2 million to about 3 million. The PEO may have a number-average molecular weight of about 5 million (all values are ±10,000 g/mol).

The PEO may include a blend of different PEOs of differing molecular weights so that the weighted-average of the component PEO's fall within the desired molecular weight range for the PEO. The PEO blend may comprise about 40% to 80% of PEO having an average molecular weight of about 5 million (e.g. POLYOX™ Coagulant; Dow Chemical) and about 60% to 10% of PEO having an average molecular weight of about 300,000 (e.g. POLYOX™ WSR-N-750; Dow Chemical). The PEO blend may comprise about 40% to 80% of PEO having an average molecular weight of about 8 million (e.g. POLYOX™ 308) and about 60% to 10% of PEO having an average molecular weight of about 300,000 (e.g. POLYOX™ WSR-N-750; Dow Chemical). The PEO blend may also advantageously contain up to about 10% (for example about 5%) by weight of a low molecular weight (i.e. MW<10,000) PEG such as PEG-100.

Suitable copolymers of PEO and PPO may have an average molecular weight of at least 5,000, preferably in the range of from 10,000 to 20,000, more preferably from 11,000 to 15,000, even more preferably from 12,000 to 13,000 and even more preferably still from 12,250 to 12,750. Without wishing to be bound by theory, the inclusion of a PEO/PPO copolymer of sufficient molecular weight is thought to further improve the lubrication properties of the shaving aid in aqueous conditions, especially in combination with a further water soluble polymer (particularly PEO), and thus prevent an undesirable feeling in use.

The PEO/PPO copolymer may advantageously be a block copolymer, preferably a tri-block copolymer having the sequence: PEO-PPO-PEO, the latter being commercially available under tradenames such as PLURACARE® (BASF) and PLURONIC® (BASF).

The PEO/PPO copolymer may have a weight ratio of PEO to PPO, of from 1000:1 to 1:1000 or from 100:1 to 1:100. The PEO/PPO copolymer is typically present at an amount of from 0.01% to 50%, preferably from 0.01% to 50%, more preferably from 2% to 40%, even more preferably from 3% to 25%, even more preferably still from 4% to 20% and most preferably from 5% to 10% by weight of the lubricating material or by weight of the shaving aid.

The shaving aid and/or water soluble polymer preferably comprises less than 5%, preferably less than 1% by weight and more preferably is/are substantially free of lathering soaps (i.e. salts of fatty $C_4$ to $C_{30}$ acids) and lathering surfactants. A lathering surfactant is defined as a surfactant which when combined with water and mechanically agitated, generates a foam or lather. Lathering surfactants may include anionic and amphoteric lathering surfactants and mixtures thereof. Anionic lathering surfactants may include sarcosinates, sulfates, sulfonate, isethionate, taurates, phosphates, lactylates, glutamates, alkali metal salts of fatty acids (i.e. soaps) having from 8 to 24 carbons, and mixtures thereof.

Azoxystrobin and Strobilurins

Azoxystrobin (FIG. 1), CAS number: 131860-33-8, IUPAC: methyl-(E)-(2-{2[6-(2-cyanophenoxy)-pyrimidin-4-iloxy]-phenyl}-3-methoxyacrylate is an agricultural fungicide belonging to the class of the strobilurins. Strobilurins are either biosynthesized by various Basidiomycete fungi such as *Strobilurus tenacellus* and *Oudemansiella mucida* or modeled after natural strobilurins and synthesized with retention of the key β-methoxyacrylate toxophore. Some synthesized strobilurins have a modified toxophore e.g. methyl methoxyiminoacetate or methyl-N-methoxycarbamate. Some synthetic strobilurins are azoxystrobin (CAS number: 131860-33-8), coumoxystrobin (CAS number 850881-70-8), dimoxystrobin (CAS number 149961-52-4), enoxastrobin (CAS number 238410-11-2), fluoxastrobin (CAS number 193740-76-0), kresoxim methyl (CAS number 143390-89-0), mandestrobin (CAS number 173662-97-0), metominostrobin (CAS number 133408-50-1), orysastrobin (CAS number 248593-16-0), picoxystrobin (CAS number 117428-22-5), pyraoxystrobin (CAS number 862588-11-2), and trifloxystrobin (CAS number 141517-21-7).

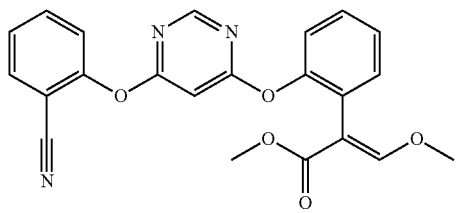

FIG. 1

Azoxystrobin and other synthetic strobilurins control a broad spectrum of plant fungal diseases and are used heavily in crop protection worldwide. Strobilurins work by inhibition of mitochondrial respiration. The specific mode of action of azoxystrobin and other strobilurins is by binding the ubiquinol oxidizing site ($Q_O$ site) in the cytochrome b complex III of the electron transport chain and blocking electron transfer between cytochrome b and cytochrome ci. Other compounds with this specific mode of action include synthetic and naturally occurring derivatives of the key β-methoxyacrylate toxophore known as oudemansins also first isolated from *Oudemansiella mucida*, synthetic and naturally occurring myxothiazols from myxobacteria such as *Myxococcus flavus*, stigmatellins from myxobacteria such as *Stigmatella aurantica* and the synthetic agricultural chemicals famoxadone and fenamidone.

Azoxystrobin as an agricultural fungicide has protectant, curative, eradicant, translaminar and systemic properties and inhibits spore germination and mycelial growth, and also shows antisporulant activity. At labelled application rates, azoxystrobin controls the numerous plant pathogens including *Erysiphe graminis, Puccinia* spp., *Lepiosphaeria nodorum, Septoria tritici* and *Pyrenophora teres* on temperate cereals; *Pyricularia oryzae* and *Rhizoctonia solani* on rice; *Plasmopara viticola* and *Uncinula necator* on vines; *Sphaerotheca fuliginea* and *Pseudoperonospora cubensis* on cucurbitaceae; *Phytophthora infestans* and *Alternaria solani* on potato and tomato; *Mycosphaerella arachidis, Rhizoctonia solani* and *Sclerotium rolfsii* on peanut; *Monilinia* spp, and *Cladosporium carpophilum* on peach; *Pythium* spp. and *Rhizoctonia solani* on turf; *Mycosphaerella* spp. on banana; *Cladosporium caryigenum* on pecan; *Elsinoë fawcetii, Colletotrichum* spp. and *Guignardia citricarpa* on citrus; *Colletotrichum* spp. and *Hemileia vastatrix* on coffee. Azoxystrobin is a solid material having low solubility in water.

Some tradenames for azoxystrobin include ABOUND FLOWABLE FUNGICIDE, Aframe, Azoxystar, Azoxyzone, AZteroid 1.65 SC Fungicide, AZURE AGRICULTURAL FUNGICIDE, Endow, QUADRIS FLOWABLE FUNGICIDE, Satori Fungicide, Strobe 2L, and Willowood Azoxy 2SC. Azoxystrobin is commercially available from for example Sigma-Aldrich (St. Louis, MO) and Ak Scientific, Inc (Union City, CA).

In the present invention, the personal care composition may contain from about 0.02% to about 10% of azoxystrobin; from about 0.1% to about 5% of azoxystrobin; from about 0.1% to about 2% of azoxystrobin; from about 0.2% to about 1% of azoxystrobin.

In the present invention, the personal care composition may contain from about 0.02% to about 10% of a strobilurin; from about 0.05% to about 2% of a strobilurin; from about 0.1% to about 1% of a strobilurin.

Carrier Matrix

The shaving aid may be a solid under ambient conditions and may comprise a carrier matrix (also referred to herein as a "carrier") that provides structural integrity to the shaving aid and may enhance the life of the lubricant by reducing its tendency to be mechanically eroded. Advantageously, the carrier may be solid at standard temperature and pressure. The lubricant may comprise from about 1% to about 50%, preferably from about 10% to about 40%, and more preferably from about 20% to about 40%, by weight of the carrier. In some examples, the carrier material may fall under the definition of hydrophobic compound as used herein, and in such a case, should be included for purposes of determining the amount by weight of the hydrophobic compound or mixture.

In some examples, the carrier may comprise a matrix polymer such as ethylene vinyl acetate (EVA). Examples of shaving aids comprising EVA may be found in, for example, U.S. Pat. Nos. 5,349,750 and 10,682,778. In other examples, the carrier may comprise a polymeric matrix material such as HIPS. Further examples of a matrix polymer may include ethyl cellulose; polycaprolactone (PCL); polyethylene, polypropylene; polystyrene; butadiene-styrene copolymer (e.g. medium impact polystyrene and HIPS); polyacetal; acrylonitrile butadiene-styrene (ABS) copolymer; and blends such as polypropylene/polystyrene blend, and mixtures thereof.

Shaving aids comprising HIPS are typically formed by extruding a mixture that is heated to approximately 200° C. and exposed to shear during extrusion. These high processing temperatures and high shear conditions may limit the stability of the lubricant and/or the viability of compatible stabilizing agents. As such, the use of a lower temperature processable polymer matrix material such as EVA, which requires a lower processing temperature of approximately 130° C., or a melt-formed composition may be preferable.

Melt-formed shaving aids may include a non-polymeric matrix or structurant as part of the carrier, in which the non-polymeric structurant has a melt temperature of less than 100° C. In some examples, the non-polymeric structurant may comprise a lipophilic structurant. Suitable lipophilic structurants for use herein include $C_{14}$ or greater, preferably $C_{14}$ to $C_{22}$, more preferably $C_{16}$ to $C_{18}$, chain length fatty acyls such as fatty acids, fatty alcohols and esters, triglycerides, waxes, and mixtures thereof. Particularly preferred are $C_{14}$-$C_{22}$ alcohols, in particular cetyl, stearyl, and behenyl alcohols and mixtures thereof.

Suitable lipophilic structurants also include natural, synthetic, and silicone waxes. As used herein, the term "wax" includes, but is not limited to, any material that is solid at 45° C., preferably at 25° C.; and are very slightly soluble in water, preferably practically insoluble in water according to the United States' Pharmacopeia (USP) definition in 31/NF 26 Vol. 2 General Notices, Page Xvii. According to that definition, this means that 1000 to 10000 parts of water are needed to dissolve 1 part solute and that more than 10,000 parts of water are needed to dissolve 1 part solute respectively.

The lipophilic structurant and/or shaving aid preferably comprises less than 5%, preferably less than 1% by weight and more preferably is substantially free of lathering soap (i.e. salts of fatty acids such as $C_4$-$C_{30}$ carboxylic acids) or lathering surfactant. A lathering surfactant is defined as a surfactant which when combined with water and mechanically agitated generate a foam or lather. Lathering surfactants include anionic and amphoteric lathering surfactants and mixtures thereof. Anionic lathering surfactants include sarcosinates, sulfates, sulfonate, isethionate, taurates, phosphates, lactylates, glutamates, alkali metal salts of fatty acids (i.e. soaps) having from 8 to 24 carbons, and mixtures thereof.

The wax may comprise natural wax, synthetic wax or mixtures thereof. Natural waxes may be plant, animal or mineral derived. Non-limiting examples of suitable natural waxes include Beeswax, *Copernicia cerifera* (Carnauba) Wax, *Euphorbia cerifera* (Candelilla) Wax, Jojoba Wax, *Oryza sativa* (Rice) Bran Wax, Lemon peel wax, Soybean wax, Sunflower wax and mixtures thereof.

Non-limiting examples of suitable synthetic waxes include Hydrogenated Jojoba Wax, synthetic and siliconyl jojoba wax, Hydrogenated Microcrystalline Wax, Microcrystalline Wax, synthetic, siliconyl and Hydrogenated Rice Bran Wax, Ceresin, Ozokerite, Paraffin, behenyl beeswax, synthetic, siliconyl and hydrogenated Beeswax, synthetic, hydrogenated and siliconyl Candelilla Wax, synthetic, hydrogenated and siliconyl Carnauba, wax, synthetic, hydrogenated and siliconyl lemon peel wax, synthetic, siliconyl and hydrogenated soybean wax, synthetic, siliconyl and hydrogenated sunflower wax and mixtures thereof. Preferred natural and synthetic waxes are Beeswax, Microcrystalline wax, Candellila wax, Ozokerite, and mixtures thereof.

Non-limiting examples of suitable silicone waxes include Stearyoxy trimethylsilane such as DC580 wax, $C_{30}$-$C_{45}$ alkyl methicone available as DC AMS-C30 Cosmetic Wax, stearyoxymethyl silane available as DC Silkywax 10, $C_{24}$-$C_{54}$ alkyl methicone such as DC ST-Wax 30, $C_{30}$-$C_{45}$ Alkyldimethylsilyl, Polypropyl-silsesquioxane, available as DC SW-8005 resin wax, and mixtures thereof.

Particularly preferred lipophilic structurants may be selected from fatty alcohols (such as cetyl alcohol, stearyl alcohol, or behenyl alcohol), microcrystalline waxes, stearyloxy trimethylsilane and mixtures thereof.

The carrier may be relatively hydrophobic to the lubricant. The benefit agent comprising azoxystrobin may preferably be incorporated into the lubricant. Where the carrier is relatively hydrophobic to the lubricant and the lubricant forms at least a partially separate phase, the azoxystrobin may partition into the lubricant phase.

Liquid Shaving Aids

The on-board liquid shaving aid composition may comprise water. In one embodiment, the composition comprises at least about 30% by weight water. In an alternate embodiment, the composition comprises at least about 40% by weight water. In an alternate embodiment, the composition comprises at least about 50%, by weight water. Compositions having high levels of water enable the device to be used without the necessity for an additional water source to apply or remove the composition from the skin after application.

Silicone Polyether Copolymer

The on-board liquid shaving aid composition may comprise from about 0.1% to about 60%, preferably from about 0.1% to about 20%, more preferably from about 0.1% to 5%, even more preferably from about 0.1% to about 1% by weight of a silicone polyether copolymer or mixtures thereof.

The silicone polyether copolymer may comprise from about 1% to 50%, preferably from 1% to 30%, by weight of polyethylene oxide, from about 20% to about 90%, preferably from 20% to 80% by weight of polypropylene oxide and from about 1% to about 20% by weight of silicone. Preferably the silicone polyether copolymer comprises at least about 40%, more preferably at least about 50%, most preferably at least about 60% by weight of polypropylene oxide. In addition, the silicone polyether copolymer preferably comprises at least about 10%, more preferably from at least about 15%, most preferably from about 15% to 30% by weight of polyethylene oxide. Furthermore, the silicone polyether block copolymer comprises from 1% to 20%, preferably 10% to 20%, more preferably about 15% by weight of silicone.

The silicone polyether copolymers may be block copolymers and may have a pendant graft structure or a linear structure. The silicone polyether block copolymer may comprise from 1% to 50%, preferably from 10% to 30%, more preferably about 20% by weight of polyethylene oxide. The silicone polyether block copolymer may comprise from 20% to 90%, preferably from 40% to 80%, more preferably from 50 to 80%. The silicone polyether block copolymer may comprise from 1% to 20%, preferably 10% to 20% by weight of silicone.

The silicone polyether block copolymer preferably has a ratio of polyethylene oxide units to polypropylene oxide units of from 3.0 to 0.1, preferably from 2.0 to 0.1, more preferably from 0.6 to 0.25. The silicone polyether block copolymer preferably has a ratio of polyethylene oxide units to polypropylene oxide units to silicone units of from 20:65:15.

The silicone polyether copolymer may have a molecular weight of from about 10000 to about 190000, more preferably from about 10000 to 15000. Suitable silicone polyether copolymers are available from Momentive under the SILWETS trademark products including L7210.

In one embodiment the on-board liquid shaving aid comprises a silicone polyether block copolymer and a water soluble polymer, at a weight ratio of from 1:8 to 8:1, preferably from 1:5 to 5:1, more preferably from 1:3 to 3:1 and even more preferably from 1:2 to 2:1.

In a preferred embodiment the silicone polyether copolymers suitable for use herein only contain repeating units of silicone, polyethylene oxide and polypropylene oxide. Silicone polyether copolymers comprising additional alkyl chains are preferably excluded.

Thickening Agent

The composition may contain one or more thickening agents, from about 0.1% to about 5%, alternatively from about 0.1% to about 4%, alternatively from about 0.25% to about 3%, by weight of the composition.

Non limiting classes of thickening agents include those selected from the following: Carboxylic Acid Polymers, Crosslinked Polyacrylate Polymers Polyacrylamide Polymers, Polysaccharides, Clays and Gums, and mixtures thereof when appropriate. In one embodiment, compositions of the present invention include a thickening agent selected from carboxylic acid polymers, crosslinked polyacrylate polymers, polyacrylamide polymers, polysaccharides, and mixtures thereof, more preferably selected from carboxylic acid polymers, polyacrylamide polymers, polysaccharides, and mixtures thereof.

Preferred thickening/suspending agents include electrolyte sensitive polymers that are shear thinning when in solution. Shear thinning is property that makes a liquid easy to spread and pump. We have found that electrolyte sensitive polymers have desired performance profiles. While not wishing to be bound by theory, the electrolyte sensitive polymers interact with the residual surfactant or electrolyte left on the skin and release the lubrication agents and/or suspended conditioning agents for spreading across the razor and across the surface of the skin. Preferred electrolyte sensitive polymers include but are not limited to: Polyacrylamide, Hydroxyethyl Acrylate/Sodium Acryloyldimethyltaurate Copolymer, Sodium Acrylate/Sodium Acryloyldimethyl Taurate Copolymer, Ammonium Polyacrylate, Sodium Acrylate/Acryloyldimethyltaurate/Dimethylacrylamide Crosspolymer, Hydroxyethyl Acrylate/Sodium Acryloyldimethyltaurate Copolymer which can be purchased from Seppic or Carboxylic Acid Polymers (Carbomers) such as Ultrez 10, Carbopol 934, Carbopol 980 and ETD 2050 which can be purchased from Lubrizol or Ammonium Acryloyldimethyltaurate/VP Copolymer, Sodium Acryloyldimethyltaurate/VP Copolymer, Ammonium Acryloyldimethyltaurate/Beheneth-25 Methacrylate Crosspolymer, which can be purchased from Clariant. The most preferred electrolyte sensitive polymer is Polyacrylamide available as Sepigel 305 (Polyacrylamide & C13-14 Isoparaffin & Laureth-7).

Surfactants

The composition may contain one or more surfactants, from about 0.1% to about 20%, alternatively from about 0.5% to about 15%, alternatively from about 1.0% to about 12%, by weight of the composition. Non limiting examples of surfactants for use herein are disclosed in McCutcheon's, Detergents and Emulsifiers, North American edition (1986), published by allured Publishing Corporation; and McCutcheon's, Functional Materials, North American Edition (1992). Preferred surfactants are nonionic surfactants/emulsifiers. Non limiting useful surfactants herein include those selected from the group consisting of alkyl glucosides, alkyl polyglucosides, polyhydroxy fatty acid amides, alkoxylated fatty acid esters, sucrose esters, alkoxylated fatty alcohols, amine oxides, and mixtures thereof. Most preferred are alkoxylated fatty alcohols and alkyl glucosides and mixtures thereof.

Liquid Phase

A solid shaving aid, particularly melt-formed shaving aids with a lipophilic structurant, may further comprise from about 10% to about 70%, preferably from about 10% to about 60%, more preferably from about 10% to about 40%, by weight of the shaving aid of a liquid phase. In one aspect, the liquid phase comprises a hydrophobic material or mixtures thereof. The liquid phase may provide a number of in use benefits such as lubrication, skin feel, skin health, and cooling sensation. The liquid phase is contained within the solid shaving aid by the lipophilic structurant.

In one example, the liquid phase may have a melting point of 45° C. or less, preferably 40° C. or less, even more preferably 30° C. or less, most preferably 25° C. or less. The melting point is determined according to ASTM D5440-93. Preferably the liquid phase and the hydrophobic material is liquid at 25° C. The use of a liquid phase enables the materials such as the lipophilic structurant to be readily added and mixed upon melting thereof. In another example, the liquid phase hydrophobic material or mixtures thereof may be very slightly soluble and have a melting point of 45° C. or less, as defined herein above, and be miscible with one another. In another example, the melting point of the mixture of liquid phase and the lipophilic structurant is preferably from 45° C. to 5° C. less than the melting point of the water soluble polymer.

Suitable liquid phase components for use herein include for example natural oils, synthetic oils, silicone oils, petrolatum, triglycerides, butters or mixtures thereof. As used herein, the term "oil" includes, but is not limited to any non-aqueous substance that is very slightly soluble, preferably practically insoluble in water according to the USP definition. Petrolatum may be considered as a lipophilic structurant or a liquid phase due to its complex mixture of component materials.

The oil may be selected from natural oil, synthetic oil, silicone oil and mixtures thereof. Non-limiting examples of suitable natural oils include Acetylated Castor Oil, Acetylated Hydrogenated Castor Oil, *Actinidia chinensis* (Kiwi), Seed Oil, *Adansonia digitata* Oil, *Aleurites moluccana* Seed Oil, *Anacardium occidentale* (Cashew) Seed Oil, *Arachis hypogaea* (Peanut) Oil, *Arctium lappa* Seed Oil, *Argania spinosa* Kernel Oil, *Argemone mexicana* Oil, *Avena sativa* (Oat) Kernel Oil, *Bertholletia excelsa* Seed Oil, *Borago officinalis* Seed Oil, *Brassica campestris* (Rapeseed) Seed Oil, *Calophyllum tacamahaca* Seed Oil, *Camellia japonica* Seed Oil, *Camellia kissi* Seed Oil, *Camellia oleifera* Seed Oil, Canola Oil, Caprylic/Capric/Lauric Triglyceride, Caprylic/Capric/Linoleic Triglyceride, Caprylic/Capric/Mystic/Stearic Triglyceride, Caprylic/Capric/Stearic Triglyceride, Caprylic/Capric Triglyceride, *Carthamus tinctorius* (Hybrid Safflower) Seed Oil, *Carthamus tinctorius* (Safflower) Seed Oil, *Carum carvi* (Caraway) Seed Oil, *Carya illinoensis* (Pecan) Seed Oil, Castor Oil Benzoate, *Chenopodium quinoa* Seed Oil, *Cibotium barometz* Oil, *Citrullus vulgaris* (Watermelon) Seed Oil, *Cocos nucifera* (Coconut) Oil, Cod Liver Oil, *Coffea arabica* (Coffee) Seed Oil, *Coix lacryma-jobi* (Job's Tears) Seed Oil, *Corylus americana* (Hazel) Seed Oil, *Corylus avellana* (Hazel) Seed Oil, *Cucumis sativus* (Cucumber) Oil, *Cucurbita pepo* (Pumpkin) Seed Oil, *Daucus carota sativa* (Carrot) Seed Oil, *Elaeis guineensis* (Palm) Kernel Oil, *Elaeis guineensis* (Palm) Oil, *Gossypium* (Cotton) Seed Oil, *Helianthus annuus* (Hybrid Sunflower) Oil, *Helianthus annuus* (Sunflower) Seed Oil, *Hippophae rhamnoides* Oil, Human Placental Lipids, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated C12-18 Triglycerides, Hydrogenated Fish Oil, Hydrogenated Lard, Hydrogenated Menhaden Oil, Hydrogenated Mink Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, *Isatis tinctoria* Seed Oil, *Juglans regia* (Walnut) Seed Oil, Lauric/Palmitic/Oleic Triglyceride, *Umnanthes alba* (Meadowfoam) Seed Oil, *Unum usitatissimum* (Linseed) Seed Oil, *Lupinus albus* Seed Oil, *Macadamia integrifolia* Seed Oil, *Macadamia ternifolia* Seed Oil, Maleated Soybean Oil, *Mangifera indica* (Mango) Seed Oil, Marmot Oil, *Melaleuca alternifolia* (Tea Tree) Leaf Oil, *Melia azadirachta* Seed Oil, *Melissa officinalis* (Balm Mint) Seed Oil, Menhaden Oil, Mink Oil, *Moringa pterygosperma* Seed Oil, *Mortierella* Oil, Neatsfoot Oil, *Nelumbium speciosum* Flower Oil, *Nigella sativa* Seed Oil, *Oenothera biennis* (Evening Primrose) Oil, *Olea europaea* (Olive) Fruit Oil, *Olea europaea* (Olive) Husk Oil, Orange Roughy Oil, *Orbignya cohune* Seed Oil, *Orbignya oleifera* Seed Oil, *Oryza sativa* (Rice) Bran Oil, *Oryza sativa* (Rice) Germ Oil, Ostrich Oil, Oxidized Corn Oil, Oxidized Hazel Seed Oil, *Papaver orientale* (Poppy) Seed Oil, *Passiflora edulis* Seed Oil, *Persea gratissima* (Avocado) Oil, *Pistacia vera* Seed Oil, Placental Lipids, *Prunus amygdalus amara* (Bitter Almond) Kernel Oil, *Prunus amygdalus dulcis* (Sweet Almond) Oil, *Prunus armeniaca* (Apricot) Kernel Oil, *Prunus avium* (Sweet Cherry) Seed Oil, *Prunus cerasus* (Bitter Cherry) Seed Oil, *Prunus persica* (Peach) Kernel Oil, *Pyrus malus* (Apple) Oil, *Ribes nigrum* (Black Currant) Seed Oil, *Ricinus communis* (Castor) Seed Oil, *Rosa canina* Fruit Oil, *Rosa moschata* Seed Oil, Salmon Oil, *Salvia hispanica* Seed Oil, *Santalum album* (Sandalwood) Seed Oil, *Sesamum indicum* (Sesame) Seed Oil, Shark Liver Oil, *Solanum lycopersicum* (Tomato) Seed Oil, Soybean Lipid, Sphingolipids, *Taraktogenos kurzii* Seed Oil, *Telphairia pedata* Oil, Vegetable Oil, *Vitis vinifera* (Grape) Seed Oil, *Zea mays* (Corn) Germ Oil, *Zea mays* (Corn) Oil mineral oil and mixtures thereof.

Suitable synthetic oils include hydrocarbons, esters, alkanes, alkenes and mixtures thereof. Non-limiting examples include isopropyl palmitate, isopropyl stearate, isohexadecane, isododecane, polyglyceryl triisostearate and mixtures thereof.

Non-limiting examples of suitable silicone oils include dimethicones (including partial esters of dimethicones and fatty acids derived from natural/synthetic oils), cyclomethicones, phenylated silicones, phenyl trimethicones, trimethyl pentaphenyl trisiloxane, silicone polyether block copolymers and mixtures thereof.

The liquid phase may contain a silicone polyether. Suitable silicone polyether copolymers are disclosed above and may comprise from about 1% to 50%, by weight of PEO, from about 20% to about 90% by weight of PPO, and from about 1% to about 20% by weight of silicone. Preferably, the silicone polyether copolymer comprises at least about 40%, more preferably at least about 50%, most preferably at least about 60%, by weight of PPO. In addition, the silicone polyether copolymer preferably comprises at least about 10%, more preferably from at least about 15%, most preferably from about 15% to 30% by weight of PEO. Furthermore, the silicone polyether block copolymer comprises from 1% to 20%, preferably 10% to 20%, more preferably about 15% by weight of silicone.

Non-limiting examples of commercially available silicone oils include Dow Corning 200 fluid, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.), the Viscasil series (sold by General Electric Company), SF 1075 methylphenyl fluid (sold by General Electric Company) and 556 Cosmetic Grade Fluid (sold by Dow Corning Corp.), Silshine 151 (sold by Momentive), PH1555 and PH1560 (sold by Dow Corning) and Silwets such as Silwets 7210, 7230 and 7220 (available from by Momentive).

Suitable triglycerides, may have the following formula:

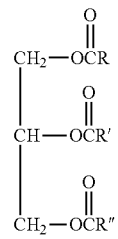

in which R, R', and R" may be the same as, or different from, one or both of the others, and in which each of R, R', and R" is a fatty acid and the triglyceride is solid at 25° C.

Suitable oils from which triglycerides may be formed include, but are not limited to, the oils listed herein. Suitable fatty acids for formation of triglycerides include, but are not limited to, Myristoleic acid, Palmitoleic acid, Sapienic acid, Oleic acid, Linoleic acid, α-Linolenic acid, Arachidonic acid, Eicosapentaenoic acid, Docosahexaenoic acid, Lauric acid ($C_{12}$), Myristic acid ($C_{14}$), Palmitic acid ($C_{16}$), Stearic acid ($C_{18}$), Arachidic acid ($C_{20}$) and mixtures thereof.

Specific sources of triglycerides suitable for inclusion herein include Shea Butter, *Theobroma cacao* (Cocoa) Seed Butter, Cocoa Butter, *Mangifera indica* (Mango) Seed Butter, Kokum Butter and mixtures thereof. Particularly preferred are shea butter, cocoa butter and mixtures thereof.

Preferred liquid phase components may be selected from capric and or caprylic triglycerides, olive oil, shea butter, cocoa butter, petrolatum, isopropyl isostearate, dimethicones, phenylated silicones, silicone polyether block copolymers and mixtures thereof. The silicone polyether block polymers are particularly advantageous as they may facilitate the dispersion of the water soluble polymer in the lipophilic structurant as discussed hereinafter and may also improve lubrication.

Optional Benefit Agents

According to the present disclosure, the shaving aid may optionally further comprise one or more additional benefit agents. The additional benefit agent(s) may include a hydrophobic compound or a hydrophilic compound. Hydrophobic benefit agents may be preferred for incorporation into the carrier of the shaving aid, as they may partition towards this phase (relative to the lubricant). Hydrophilic benefit agents may be preferred for incorporation into the lubricant.

In one example, the shaving aid may comprise from 1% to 40%, preferably from 5% to 40%, more preferably from about 10% to about 40%, even preferably from about 12% to about 30% by weight of a hydrophobic compound and or mixtures thereof. Suitable hydrophobic compounds include natural oils, waxes, and/or fats; synthetic waxes or oils; triglycerides; skin active agents; sensates; fragrance oils; silicones; and mixtures thereof. The hydrophobic compound can provide a number of in use benefits such as lubrication, skin feel, skin health, and cooling sensation. Any of the oils discussed as components of the liquid phase (above) may also be incorporated as an optional benefit agent.

The hydrophobic compound may comprise skin active agents such as, but not limited to, oil soluble vitamins, such as vitamin E derivatives, including vitamin E acetate and tocopherol nicotinate; oil-soluble vitamin A derivatives, such as retinyl palmitate; lanolin; ceramides; sterols and sterol esters; salicylic acid; camphor; eucalyptol; essential oils; peppermint oil; ISO E SUPER® [(1-(1,2,3,4,5,6,7,8-octahydro-2,3,8,8-tetramethyl-2-naphthalenyl)ethanone] (International Flavors & Fragrances Inc.); and mixtures thereof.

In some examples, the hydrophobic compound may comprise one or more sensates. Among synthetic coolants, many are derivatives of, or are structurally related to, menthol, i.e., containing the cyclohexane moiety, and derivatized with functional groups including carboxamide, ketal, ester, ether, and alcohol. Non-limiting examples include menthyl ethyl-amido oxalate (under the tradename FRESCOLAT® X-COOL® from Symrise), menthyl lactate (such as FRESCOLAT® ML Natural available from Symrise), and menthyl pyrrolidone carboxylate, also known as menthyl PCA (under the tradename QUESTICE® from Givaudan).

Hydrophobic compounds may be selected from capric and or caprylic triglycerides, grape seed oil, olive oil, microcrystalline wax, shea butter, cocoa butter, lanolin, essential oil, peppermint oil, isohexadecane, petrolatum, silicone polymers including waxes and oils (selected from dimethicones, phenylated silicones and mixtures thereof), and mixtures thereof.

Hydrophilic benefit agents include stabilizing agents such as anti-oxidants (such as RALOX 35) and/or chelants (such as EDTA, citric acid) which may help ensure the stability of the water soluble polymer during manufacture and/or storage and/or use of the shaving aid.

2-Pyridinol-N-oxide materials may also be suitable for use in this invention and which may enhance the benefit(s) conferred by the azoxystrobin or other strobilurins. Suitable 2-Pyridinol-N-oxide materials include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

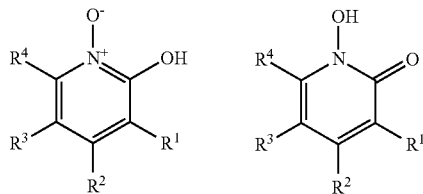

where $R^1$, $R^2$, $R^3$, $R^4$ groups are independently selected from the group consisting of H, Cl, Br, I, F, NO, $NO_2$, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $^+N(R^7R^8R^9R^{10})$, and $1/q\ M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide material is a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1. In other aspects, the 2-pyridinol-N-oxide material is a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

In certain aspects, the 2-pyridinol-N-oxide material is the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, $\frac{1}{2}Mg^{2+}$, or $\frac{1}{2}Ca^{2+}$, substituted ammonium, such as $C_1$-$C_6$ alkanolammonium, mono-ethanolamine (MEA), tri-ethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

In certain aspects, the 2-pyridinol-N-oxide material is of a substituted or unsubstituted 2-pyridinol-N-oxide material. Salts for use herein include those formed from the polyvalent metals barium, bismuth, strontium, copper, zinc, cadmium, zirconium and mixtures thereof.

In some aspects, the 2-pyridinol-N-oxide material is selected from the group consisting of: 6-hydroxy-3-pyridinesulfonic acid, 1-oxide (CAS 191672-18-1); 2-hydroxy-pyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4, 6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-

72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, MO) and/or Aces Pharma (Branford, CT).

In certain aspects, the 2-pyridinol-N-oxide material is a 2-pyridinol-N-oxide selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide material is a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, MO), Princeton Building Blocks (Monmouth Junction, NJ), 3B Scientific Corporation (Libertyville, IL), SynFine Research (Richmond Hill, ON), Ryan Scientific, Inc. (Mt. Pleasant, SC), and/or Aces Pharma (Branford, CT).

In certain aspects, the 2-pyridinol-N-oxide material is a 2-pyridinol-N-oxide material or tautomer thereof according to the formula(s) below:

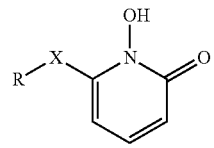

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

In certain aspects, the 2-pyridinol-N-oxide material is a 2-pyridinol-N-oxide material or tautomer thereof according to the formula(s) below:

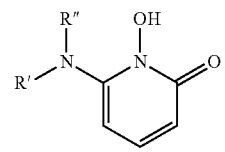

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt, piroctone olamine.

In the present invention, the personal care composition may contain from about 0.1% to about 10% of a substituted or unsubstituted 2-pyridinol N-oxide material. Alternatively, the personal care composition may contain from about 0.3% to about 3% of a substituted or unsubstituted 2-pyridinol N-oxide material. Alternatively, the personal care composition may contain from about 0.5% to about 2% of a substituted or unsubstituted 2-pyridinol N-oxide material.

In some examples, the shaving aid may optionally comprise any other ingredients commonly found in commercially available shaving aids. The shaving aid may therefore contain other conventional shaving aid ingredients, including water-swellable release enhancing agents such as cross-linked polyacrylics (e.g., 2% to 7% by weight), colorants, skin feel/care actives such as water soluble cationic polymers, surfactants, soaps (including interrupted soaps), antioxidants, preservatives, emollients, beard softeners, astringents, medicinal agents, plasticizers, additional lubricants, depilatories/keratolytic materials, tackifiers, skin-soothing agents, fragrances, compatibilizers, anti-inflammatory agents, antipruritic/counterirritant materials, and mixtures thereof. These ingredients may fall under the definition of hydrophobic compounds as used herein and should be included as such in determining the amount of the hydrophobic compound(s).

Compositions

TABLE 1

| Comp. No. | Composition |
|---|---|
| 1 | A shaving aid, comprising: a lubricant; and a benefit agent comprising azoxystrobin |
| 2 | In one aspect, of the composition 1 the shaving aid comprises about 0.1% to about 5%, by weight of the shaving aid, of azoxystrobin. |
| 3 | In one aspect, of the composition 1 or 2 of Table 1 the lubricant comprises at least 50% polyethylene oxide. |

TABLE 1-continued

| Comp. No. | Composition |
|---|---|
| 4 | In one aspect, of the compositions 1-3 of Table 1 the azoxystrobin is disposed at least partly within the lubricant. |
| 5 | In one aspect, of the compositions 1-4 of Table 1 the shaving aid comprises a matrix polymer. |
| 6 | In one aspect, of the composition 5 of Table 1 the matrix polymer is ethylene vinyl acetate. |
| 7 | In one aspect, of the composition 5 of Table 1 the matrix polymer has a glass-transition temperature less than 130° C. |
| 8 | In one aspect, of the compositions 1-4 of Table 1 the shaving aid comprises a non-polymeric matrix. |
| 9 | In one aspect, of the composition 8 of Table 1 the non-polymeric matrix has a melt-temperature less than 100° C. |
| 10 | In one aspect, of the compositions 1-4 of Table 1 the shaving aid is a pressed pellet. |
| 11 | In one aspect, of the compositions 1-4 of Table 1 the shaving aid is a liquid. |
| 12 | A hair removal device comprising a shaving aid of compositions 1-11. |
| 13 | In one aspect, the hair removal device of composition 12 is a razor. |
| 14 | In one aspect, the hair removal device of composition 12-13 includes is a liquid shaving aid contained within a reservoir on-board the hair removal device. |
| 15 | In one aspect, the hair removal device of composition 14 the shaving aid is dispensed adjacent to the hair removal head. |
| 16 | In one aspect, the hair removal device of composition 14 is dispensed opposite to the hair removal head. |
| 17 | In one aspect, the hair removal device of composition 13 the shaving aid is a solid and contained within a container on-board the hair removal device. |
| 18 | In one aspect, the shaving aid of compositions 1-11 also include a 2-Pyridinol-N-oxide material. |
| 19 | In one aspect, the hair removal device of compositions 12-17 also include a shaving aid of composition 18. |

Methods of Manufacture/Processing

The shaving aid may be formed using any method known in the art such as molding (including melt-forming), pressing, impregnation, spray-coating, calendaring, and extrusion. All of the components of the shaving aid can be blended prior to molding or extrusion. For best results, it is preferred that the components are dry. In summary, the method comprises the steps of providing a feed comprising the lubricant, the antioxidant, the chelant, the carrier, and/or additional optional ingredients and forming the mixture by molding, pressing, impregnating, spray-coating, calendaring, and/or extruding the mixture to form a solid shaving aid. Additional optional steps may be included depending on the process of manufacture that is utilized, e.g., heating the feed to an appropriate processing temperature, mixing and shearing. The shaving aid may be formed separately from the hair removal device or formed directly onto a portion of the hair removal device, including the hair removal head.

Extrusion

The shaving aid may be extruded. Extrusion is particularly preferred where the shaving aid comprises a carrier which is a matrix polymer such as HIPS or EVA. The extrusion process generally consists of blending the components, which generally requires that the carrier be melted with heat. The benefit agent comprising the azoxystrobin may be pre-mixed into at least one of the other components or added separately.

The blended components may be extruded (e.g. which applies shear), such as through a HAAKE™ System 90 (Thermo Scientific) ¾ inch (~1.91 cm) diameter extruder with a barrel pressure of about 1000 psi to 2000 psi (~6.90 MPa-13.8 MPa), a rotor speed of about 10 rpm to 50 rpm, and a temperature of about 150°-185° C. and a die temperature of about 170°-185° C. Alternatively, a 1¼ inch (~3.18 cm) single screw extruder may be employed with a processing temperature of 175°-200° C., preferably 185°-190° C., a screw speed of 20 rpm to 50 rpm, preferably 25 rpm to 35 rpm, and an extrusion pressure of 1800 psi to 5000 psi (~12.4-34.5 MPa), preferably 2000 psi to 3500 psi (~13.8 MPa-24.1 MPa). The extruded shaving aid may be air cooled to about 25° C.

The shaving aid may be injection molded. To injection mold the shaving aid, the blended components may first be extruded into pellets. This can be done on a 1¼ or 1½ inch (~3.18 cm or 3.81 cm) single screw extruder at a temperature of 120° C.-180° C., preferably 140° C.-150° C., with a screw speed of 20 rpm to 100 rpm, preferably 45 rpm to 70 rpm. The pellets are then molded (with or without re-melting) in either a single material molding or multi-material molding machine, which may be single cavity or multi-cavity, and optionally equipped with a hot-runner system. The process temperature can be from 165° C. to 250° C., preferably from 180° C. to 225° C. The injection pressure should be sufficient to fill the part completely without excess flashing. Depending on the cavity size, configuration and quantity, the injection pressure can range from 300 to 2500 psi (~2.07-17.2 MPa). The cycle time is dependent on the same parameters and can range from 3 to 30 seconds, with the optimum generally being about 6 to 15 seconds.

The matrix polymer is generally heated above its glass transition temperature. The matrix polymer may be chosen to allow for lower processing temperatures. For example, the matrix polymer may be EVA and may have a glass-transition temperature less than 130° C.

The blended components may be extruded through a Rondol 18, 18 mm diameter extruder with a barrel pressure of about 500-1000 psi, a rotor speed of about 10 to 50 rpm, and a temperature of about 100°-160° C. and a die temperature of about 100°-160° C. Alternatively, a 1½ inch single screw extruder may be employed with a processing temperature of 100°-160° C., preferably 110-130° C., a screw speed of 20 to 50 rpm, preferably 25 to 50 rpm, and an extrusion pressure of 1800 to 7500 psi, preferably 4000 to 6500 psi. Other extrusion conditions can also be employed. The extruded strip is cooled to about 25° C. To injection mold the strips it is preferred to first extrude the powder blend into pellets. This can be done on a 1¼ or 1½ inch single screw extruder at a temperature of 100°-140° C., preferably 110°-130° C., with a screw speed of 20 to 100 rpm, preferably 45 to 70 rpm. The pellets are then molded in either a single material molding or multi-material molding machine, which may be single cavity or multi-cavity, optionally equipped with a hot-runner system. The process temperature can be from 100° to 185° C., preferably from 110° to 145° C. The injection pressure should be sufficient to fill the part completely without flashing. Depending on the cavity size, configuration, and quantity, the injection pressure can range from 300 to 2500 psi. The cycle time is dependent on the same parameters and can range from 3 to 30 seconds, with the optimum generally being about 6 to 15 seconds. In one embodiment, one or more feeds can be preheated or they can be fed in at ambient temperature. Methods for forming extruded shaving aids comprising EVA are further described in U.S. Pat. No. 5,349,750 and U.S. Patent Application Publication Nos. 2017/0334082 and 2018/0117780.

Melt Formed

The shaving aid may be manufactured using a melt formed process. In such processes, the ingredients are heated and stirred until melted. The molten material is then transferred into a mold, and the temperature is reduced. Optionally, pressure may be applied. The shaving aid is removed from the mold upon cooling.

The ingredients may be premixed in one fashion or another. The process may include combining a lipid phase (e.g. comprising the lipophilic structurant) and a liquid phase as previously discussed. The lipid phase and/or the liquid phase may include the lubricant, or the lubricant may be added as a separate phase. The benefit agent comprising the azoxystrobin may be pre-mixed into at least one of the other components or added separately.

The lipid phase may comprise a lipophilic structurant. The lipid phase may comprise from about 10% to about 70%, preferably from about 10% to 60%, more preferably from about 20% to about 40%, even more preferably from about 25% to about 35% by weight of the shaving aid of a lipophilic structurant.

Pressing

In another example, the shaving aid may be provided in the form of a tablet, bar or other solid form comprising compressed powder. For such examples, the shaving aid may be manufactured whereby the lubricant and other solid dry components are provided as particulates and mixed. The benefit agent comprising the azoxystrobin may be pre-mixed into at least one of the solid dry components or added separately. The particulate material(s) is solid at 25° C. and preferably has a melting point of 30° C. or more. The shaving aid thus may comprise from 10% to 90% by weight of a particulate material(s) of the lubricant.

The shaving aid may comprise from 40% to 90% lubricant. The shaving aid may be formed by compression such as cold-compression as disclosed in US2011/0041865.

The shaving aid may comprise greater than 90% of the lubricant up to and including 100% of the lubricant (absent the preserving agent(s) of the present invention). The shaving aid may be formed by compression such as ultrasonic-compression as disclosed US2012/0023763.

The terms "compression," "compression molding," and "compression compaction" as used herein refer to a process by which the bulk density of a particulate or powder is reduced to form a solid tablet by the application of pressure. Typically, this is performed without the application of external shear force or heat. Preferably the compression compaction is conducted below the melting point of at least one, preferably all, the particulate components, preferably at an ambient temperature of 25° C. As such, the particulates retain their integrity after the compression process and are typically visible by the naked eye after the compression process is completed.

In certain examples, additional energy sources such as heat or ultrasonic energy may be applied during or after compression to increase inter-particulate bonding and increase the rigidity of the resulting shaving aid. Application of additional energy preferably does not result in any substantial melting of the particulate material. Preferably, this method does not require an extrusion or injection molding step or the application of energy sources such as heat.

The shaving aid may thus be provided in the form of a compressed solid formed from particulates. Preferably, the particulates have an average particle size distribution of from about 50 to 1250 microns and preferably from about 300 to 1250 microns, more preferably about 1000 microns. Alternatively, the particulate size is such that 90% of particles pass through a 20 mesh screen, i.e., 90% of particles are less than 841 microns in diameter. The shaving aid is compressed preferably directly into a preform or container with a compression force of typically greater than 1 KN. This may be achieved using any method and equipment known in the art such as a die press. The bulk density of the particulate material prior to compression is typically about 300 to 600 $kg/m^3$ and increases to about 1000 to 1200 $kg/m^3$ following compression. Bulk density thus may be increased by about 200% to about 400% after the compression. Without wishing to be bound by theory, it has been found that the use of particulate compression manufacturing, preferably cold particulate compression (i.e. at 25° C. or less), to form the shaving aid enables highly lubricous components to be incorporated therein without negatively impacting the water solubility and swelling performance of the water soluble polymer. This also allows flexibility in the size of the resulting shaving aid to be used for multiple razor cartridges.

Liquid Compositions

Liquid compositions are made by conventional means for mixing liquids. Where the liquid composition is a single-phase composition the ingredients, generally, are simply combined and stirred. Where the liquid composition is a multi-phase liquid, the ingredients comprising individual phases are mixed and then combined. Details of the compounding and mixing of the liquid compositions is included, below, with the compositional details.

Examples

The following example formulations of shaving aids in accordance with the present disclosure are made according to Tables 3-5 below. All values are w/w %.

Extruded Compositions with Matrix Polymer

The compositions listed in Table 2 are made via the corresponding extrusion process described above. For the polymer-matrix examples where EVA is the polymeric matrix, the extrusion temperature is 120° C. For examples where HIPS is the polymeric matrix, the extrusion temperature is 185° C.

TABLE 2

| | Example 1 | Example 2 | Example 3 |
|---|---|---|---|
| Polyox N750[1] | — | 24.6 | 36.1 |
| Polyox 308 | 50 | — | — |
| Polyox Coagulant | — | 36.9 | 24.15 |
| Ethylene Vinyl Acetate | 39 | 27 | — |

TABLE 2-continued

|  | Example 1 | Example 2 | Example 3 |
|---|---|---|---|
| HIPS | — | — | 27.5 |
| Carbowax 4600[1] | 5 | 5 | 5 |
| Polycaprolactone | 5 | 5 | 5 |
| Azoxystrobin | 0.5 | 1 | 2 |
| Irganox 1010 | 0.5 | 0.5 | 0.25 |

[1]Available from Dow

Melt-Formed Compositions with Non-Polymeric Matrix

The compositions listed in Table 3 are made via the corresponding melt-formed process described above.

TABLE 3

|  | Example 1 | Example 2 | Example 3 | Example 4 | Example 5 |
|---|---|---|---|---|---|
| Behenyl Alcohol | 30 | 30 |  |  |  |
| Stearyl alcohol |  |  | 30 | 30 | 30 |
| Petrolatum | 39.5 | 32.5 | 40 |  | 30 |
| Mineral Oil |  |  |  | 40 |  |
| PEO | 27 | 25.5 |  | 28 | 28.5 |
| Brij CS20[1] |  | 5 | 28 |  | 5 |
| Lauric Acid |  | 5 |  |  | 5 |
| Dowsil ES5600[2] | 0.5 | 0.5 |  |  |  |
| BHT | 1 | 1 | 1 | 1 | 1 |
| Azoxystrobin | 2 | 0.5 | 1 | 1 | 0.5 |

[1]Available from Croda Industrial Chemicals
[2]Available from Dow Chemical

Pressed Compositions

The compositions listed in Table 4 are made via the corresponding pressing process described above.

TABLE 4

|  | Example 1 | Example 2 |
|---|---|---|
| Cetyl alcohol | 15 | 5 |
| PEO | 57 | 88.5 |
| Magnesium Stearate | 2 |  |
| Sodium Carboxymethyl cellulose | 25 |  |
| Hydroxypropylmethyl cellulose |  | 5 |
| Ralox 35 [1] | 0.5 | 0.5 |
| Azoxystrobin | 0.5 | 1 |

[1] Available from Raschig

Multi-Phase Liquid Compositions

The compositions listed in Table 5 are made via the corresponding liquid process described.

TABLE 5

|  | Example 1 | Example 2 |
|---|---|---|
| Phase A |  |  |
| Water | 8.00 | 9.00 |
| Brij 35 (Laureth-23)[1] | 2.00 | 2.20 |
| Phase B |  |  |
| Petrolatum White | 12.00 | 4.00 |
| Wickenol 111 (Isopropyl Palmitate) | — | 10.00 |
| Mineral oil | 10.0 | — |
| Phase C |  |  |
| Water | qs | qs |
| Azoxystrobin | 0.5 | 1 |
| Brij 35 (Laureth-23)[1] | 4.40 | 4.40 |
| Glycerin | 10.0 | 5.00 |
| Natrosol 250 HHR[2] (Hydroxyethylcellulose) | 0.50 | 0.50 |
| PEG-90M (Polyox Wsr-301)[3] | — | 0.20 |
| Sepigel 305 (Polyacrylamide & C13-14 Isoparaffin & Laureth-7)[4] | 1.60 | — |
| Carbomer (Carbopol Ultrez 10)[5] | — | 0.35 |
| Sodium Hydroxide (50% Solution) | — | 0.85 |
| Phase D |  |  |
| Fragrance | 2.50 | 2.50 |
| Disodium EDTA | 0.10 | 0.10 |
| DMDM Hydantoin | 0.30 | 0.20 |
| Iodopropynyl Butylcarbamate | 0.09 | 0.09 |
| Phenoxyethanol | 0.50 | 0.50 |
| Total | 100.00 | 100.00 |

[1]Available from Croda
[2]Available from Ashland Specialty Chemical
[3]Available from Dow
[4]Available from SEPPIC
[5]Available from Lubrizol The above examples in Table 5 are made according to the method below.
1. Weigh out water from Phase C into a vessel sufficient to hold the entire batch and heat to above 60 C while mixing. Add remaining materials while allowing for sufficient mixing, melting, dispersion and/or incorporation between each addition to form a uniform mixture.
2. Weigh out the water from Phase A into a separate vessel and heat contents to above 60 C while mixing.
3. Add remaining materials from Phase A and mix until fully melted and dissolved.
4. Weigh out the materials from Phase B into a separate vessel and heat contents to above 60 C while mixing.
5. Apply high-shear to Phase A using homogenizer/mill while slowly adding the contents of Phase B to the vessel containing Phase A. Continue homogenization after the addition has been completed.
6. Stop homogenization of the combined Phases A and B, and add mixture to the vessel containing Phase C.
7. Adjust pH for formulas containing Carbomer using Sodium Hydroxide
8. Begin cooling batch to below 45 C while continuing to mix
9. Once below 45 C, add the materials in Phase D in succession and continue mixing
10. Cool to below 30 C and QS with water Single-Phase Liquid Compositions The compositions listed in Table 6 are made via the corresponding liquid process described.

TABLE 6

| Ingredient | Example 1 |
|---|---|
| Deionised water | Qs |
| Carbopol ETD 2020[1] | 0.500 |
| DMDM Hydantoin and butyl carbamate | 0.400 |
| Glycerine | 1.000 |
| Panthenol | 0.500 |
| Disodium EDTA | 0.250 |
| Perfume | 0.150 |
| Silwet L7210 | 1.00 |
| Triethanolamine | 0.680 |

[1]Supplied by Lubrizol

The above example in Table 6 is made according to the method below.

Heat the water and glycerine while stirring (at about 200 rpm) to 55° C. Then add disodium EDTA and continue stirring at 55° C. until it is fully dissolved. Then add and carefully disperse the Carbopol while stirring (at about 250 rpm). Remove from the heat and add the triethanolamine and continue to stir at 200 rpm. Then add the panthenol while continuing to stir at 200 rpm. When the temperature reaches 45° C., add the DMD Hydantoin/butyl carbamate and continue to stir for 5 minutes. Lastly, add the Silwet L7210 and perfume and continue stirring for about 5 minutes, followed by 1 minute of high shear (at about 7500 rpm). The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair removal device comprising a hair removal head and a solid shaving aid, wherein the solid shaving aid comprises:

a. a solid carrier matrix, wherein the solid carrier matrix comprises a matrix polymer;

b. a solid water soluble lubricant dispersed in said solid carrier matrix;

c. a solid benefit agent comprising azoxystrobin incorporated into the solid water soluble lubricant; and d. a 2-pyridinol-N-oxide material; wherein the 2-pyridinol-N-oxide material enhances the benefits conferred by the azoxystrobin.

2. The hair removal device of claim 1, wherein the hair removal device is a razor.

3. The hair removal device of claim 1, wherein the solid water soluble lubricant comprises polyethylene oxide or a copolymer thereof.

4. The hair removal device of claim 1, wherein the matrix polymer has a glass-transition temperature less than 130° C.

5. The hair removal device of claim 1, wherein the matrix polymer comprises ethylene vinyl acetate.

6. The hair removal device of claim 1, wherein the lubricant is at least partially phase separated from the solid carrier matrix.

7. The hair removal device of claim 1, wherein azoxystrobin is present in an amount of from about 0.1% to about 5%, by weight of the shaving aid.

8. The hair removal device of claim 1, wherein the 2-pyridinol-N-oxide material is present in an amount of from about 0.1% to about 10%, by weight of the shaving aid.

* * * * *